United States Patent [19]

Hutton

[11] Patent Number: Plant 5,257

[45] Date of Patent: Jul. 10, 1984

[54] ROSE PLANT—MEICOSABRI VARIETY

[75] Inventor: Steven B. Hutton, West Grove, Pa.

[73] Assignee: The Conard-Pyle Company, West Grove, Pa.

[21] Appl. No.: 437,747

[22] Filed: Oct. 29, 1982

[51] Int. Cl.[3] ..... A01H 5/00

[52] U.S. Cl. ..... Plt./24

[58] Field of Search ..... Plt./24

*Primary Examiner*—Robert E. Bagwill

*Attorney, Agent, or Firm*—Burns, Doane, Swecker & Mathis

[57] ABSTRACT

A new and distinctive rose of the Floribunda Class is provided which resulted as a sport of the Meigandor variety (U.S. Plant Pat. No. 4,520). The new variety forms highly attractive double blossoms which differ in coloration from those of the parent variety. More specifically, the buds of the new variety are of a deep orange-gold coloration and the flowers are of a medium yellow coloration. Additionally, the buds of the new variety are more tapered in contrast to the more squared bud shape of the parent, and the stems tend to be of a larger caliper and of a greater length than those of the parent. The new variety is well adapted to forcing in greenhouses to yield an abundance of well-formed long lasting blossoms.

1 Drawing Figure

SUMMARY OF THE INVENTION

The new variety was discovered by me during the winter of 1979 as a bud sport growing on a rose-plant of the Meigandor variety (U.S. Plant Pat. No. 4,520) in a greenhouse of The Conard-Pyle Company at West Grove, Penna. In view of its distinctive appearance buds were removed from the sporting branch and were budded onto the understock *Rosa indica.* Three plants of the new variety were obtained, and buds from these three plants were again budded onto the understock *Rosa indica.* This asexual reproduction was repeated over several succeeding generations in order to increase the number of plants of the new variety and to observe and to confirm its distinctive characteristics. As a result of this work the characteristics of the new variety were found to be fully transmissible by such vegetative propagation.

It was found that the resulting new and distinct variety of Floribunda rose-plant can be characterized by the fact that from the physical point of view, the new variety is a sport of the Meigandor variety (U.S. Plant Pat. No. 4,520) and differs from the parent in the coloration of the buds and blossoms with the buds being of orange-gold coloration and the fully open blossoms being of medium yellow coloration, the buds are more tapered in contrast to the more squared bud shape of the parent, and the stems tend to be of larger caliper and of greater length than those of the parent, and from the biological point of view the new variety has vigorous vegetation, is well adapted to greenhouse forcing, and produces an abundance of well-formed long lasting flowers.

The rose-plant of the new variety has been named the Meicosabri variety.

BRIEF DESCRIPTION OF THE PHOTOGRAPHS

The accompanying photographs show, as nearly true as it is reasonably possible to make the same in color illustrations or this character, typical specimens of the cut flowers and foliage grown in October under two sheets of polyethylene at West Grove, Penna.

DETAILED DESCRIPTION

The plant described was grown under two sheets of polyethylene at West Grove, Penna.

The chart utilized in the identification of the colors is that of The Royal Horticultural Society (R.H.S. Colour Chart).

Class: Floribunda.

Stems:

*Length.*—The length of the cut stems averages approximately 10 percent longer than the Meigandor parent, i.e. averages approximately 45 to 55 cm.

*Diameter.*—The caliper tends to be larger than that of the Meigandor parent variety.

*Color.*—Substantially similar to that of the parent. Young stems: before the bud is formed the stems are light green. Mature wood: Green Group 137C.

*Prickles.*—Substantially similar to those of the parent. Shape — Upper edge: straight, inflected towards the base. Shape — lower edge: concave. Base: elliptic. Size: medium. Quantity: often numerous. Color-on young stems: initially reddish purple, eventually becoming Straw Yellow. Color-on mature wood: Havana Brown.

Leaves:

*Stipules.*—Adnate, pectinate, they are narrow, small and serrulated.

*Petioles.*—Inner surface: the deeper part of the groove is light green, the edges slightly glandular.

*Folioles.*—Number: 3 or 5 or 7. Shape: ovate; base obtuse and apex obtuse to acute. Margins: serrate. Size: varies widely with age and position on stem; approximately 3.5 to 6.8 cm. in length and approximately 1.9 to 4.6 cm. in width.

*Color.*—Young foliage, upper surface: Green Group 137C. Young foliage, under surface: Greyed-Green Group 191C. Mature foliage, upper surface: Green Group 137A. Mature foliage, under surface: Greyed-Green Group 191B.

Inflorescence:

*Number of flowers.*—Generally one per stem when grown in a greenhouse.

*Peduncle.*—Light green, with an average length of approximately 7.5 to 8.5 cm.

*Sepals.*—Whitish and tomentous inside and light green outside. Tapered and narrow tip. The edges occasionally have a few appendages.

*Bud.*—Shape: tapered and pointed, in contrast to the more squared bud configuration of the parent variety. Length: approximately 3.8 cm. on average. Color: when opening: the inside of the petals between Yellow-Orange Group 21A and 21B, and the outside of the petals Yellow-Orange Group 20A.

*Flower.*—Shape: fully double with approximately 25 to 30 petals. Diameter: approximately 9.0 to 11.0 cm. on average when fully open. Color: When one-half open—Inside of petals: between Yellow Group 13A and 13B. Outside of petals: Yellow Group 12A. When fully open—Inside of petals: between Yellow Group 8B and 8C. Outside of petals: Yellow Group 6D. Fragrance: virtually none. Lasting quality: very long, on the plant as well as when cut. Corolla: Petals—Texture: leathery. Shape: Wide base, the tip is rounded. There may be some short petals in center which are not always entire. When one-half open the petals tend to possess a deep groove down the center which gives the petals a somewhat "V" shape. The opened petals tend to reflex primarily from the base. Shedding petals: the petals drop off cleanly. Stamens—Number: approximately 50 on the average. Anthers: normal and yellow. Filaments: long and yellow. Pistils—Number: approximately 25 to 30 on an average. Stigmas: yellow; reach the same height as the anthers. Styles: long, whitish at the base, and fuchine at tip. Receptacle: light green, hairless, when cut longitudinally, wide and in the shape of a funnel.

Development:

*Vegatation.*—Vigorous.

*Blossoming.*—Continuous in greenhouse.

*Resistance to disease.*—Average.

I claim:

1. A new and distinct variety of Floribunda rose-plant characterized by the fact that from the physical point of view, the new variety is a sport of the Meigandor variety (U.S. Plant Pat. No. 4,520) and differs from the parent in the coloration of the buds and blossoms with the buds being of orange-gold coloration and the fully open blossoms being of medium yellow coloration, the buds are more tapered in contrast to the more squared bud shape of the parent, and the stems tend to be of larger caliper and of greater length than those of the parent, and from the biological point of view the new variety has vigorous vegetation, is well adapted to greenhouse forcing, and produces an abundance of well-formed long lasting flowers, substantially as shown and described.

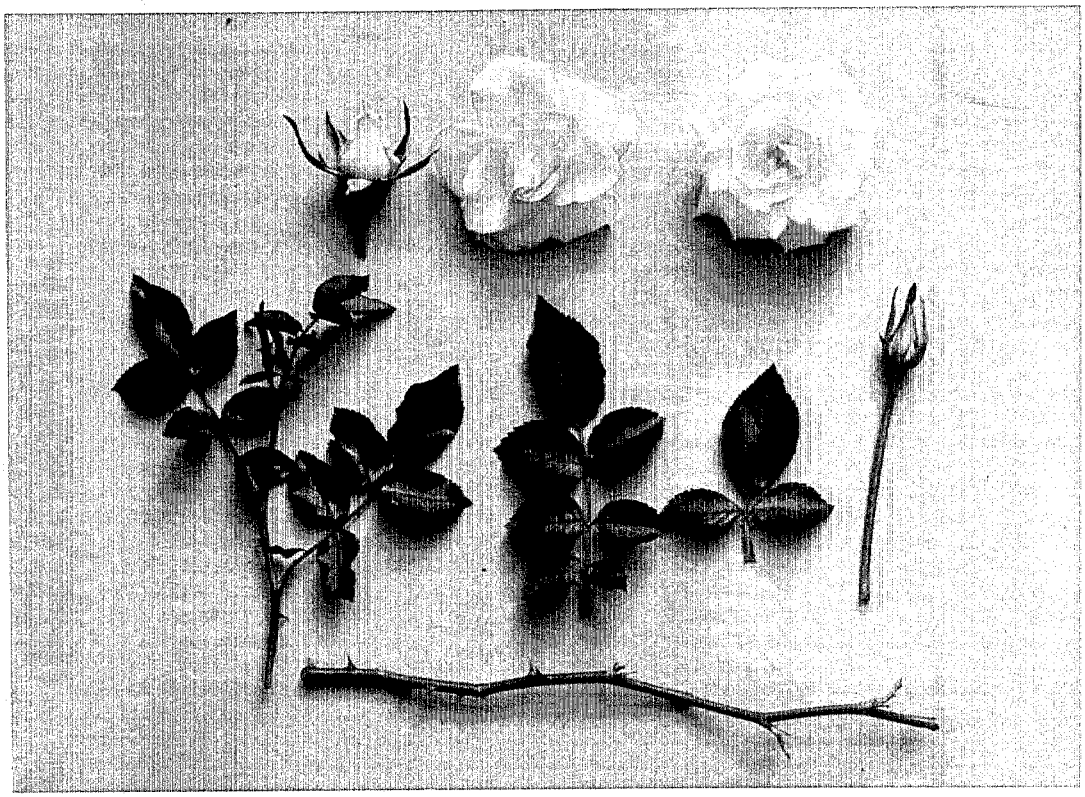

* * * * *